United States Patent
Weber

(10) Patent No.: US 9,212,973 B2
(45) Date of Patent: Dec. 15, 2015

(54) DEVICE FOR SIMULATING CRASH SCENARIOS

(71) Applicant: MESSRING Systembau MSG GmbH, Krailling (DE)

(72) Inventor: Robert Weber, Unterzeitlbach (DE)

(73) Assignee: MESSRING SYSTEMBAU MSG GMBH, Krailling (DE)

( * ) Notice: Subject to any disclaimer, the term of this patent is extended or adjusted under 35 U.S.C. 154(b) by 134 days.

(21) Appl. No.: 14/088,974

(22) Filed: Nov. 25, 2013

(65) Prior Publication Data

US 2014/0144207 A1    May 29, 2014

(30) Foreign Application Priority Data

Nov. 26, 2012 (DE) .......................... 10 2012 023 076

(51) Int. Cl.

| | |
|---|---|
| *G01N 3/08* | (2006.01) |
| *G01M 17/007* | (2006.01) |
| *G01N 3/307* | (2006.01) |
| *G01M 10/00* | (2006.01) |

(52) U.S. Cl.
CPC ........... *G01M 17/0078* (2013.01); *G01M 10/00* (2013.01); *G01N 3/307* (2013.01)

(58) Field of Classification Search
CPC ... G01N 3/307; G01N 3/303; G01M 17/0078; G01M 10/00; G09B 9/08
USPC .................................. 73/12.07, 12.04, 12.01
See application file for complete search history.

(56) References Cited

U.S. PATENT DOCUMENTS

| | | | | |
|---|---|---|---|---|
| 6,077,078 | A | * | 6/2000 | Alet et al. .................. 434/55 |
| 6,902,488 | B2 | * | 6/2005 | Hashimoto et al. ............. 472/59 |
| 2004/0230394 | A1 | * | 11/2004 | Saari et al. .................... 702/113 |

FOREIGN PATENT DOCUMENTS

| | | |
|---|---|---|
| DE | 19857429 A1 | 6/2000 |
| DE | 19805512 B4 | 9/2004 |
| DE | 10118682 B4 | 6/2005 |
| DE | 102005010189 B3 | 11/2006 |
| DE | 102007042775 A1 | 3/2009 |
| DE | 102007056572 A1 | 5/2009 |
| EP | 2098850 A2 | 9/2009 |
| JP | 2007114084 A | 5/2007 |

* cited by examiner

*Primary Examiner* — Lisa Caputo
*Assistant Examiner* — Nathaniel T Woodward
(74) *Attorney, Agent, or Firm* — The Webb Law Firm

(57) ABSTRACT

A device for simulating the effects of a crash on a test object is provided. The device includes a sled adapted to be accelerated in the longitudinal direction. The sled comprises a lower part and an upper part supported thereon used as a carrier for the test object. The lower part and the upper part have actuators provided between them, whereby pitching and yawing movements of the upper part can be generated. The upper part is, on an impact-side front end of the sled, propped against the lower part by means of a coupling rod which is rotatably coupled on both sides thereof, at least five actuators provided between the lower part and the upper part, the upper part being supported on the lower part via the actuators and the coupling rod such that a rolling movement of the upper part can additionally be generated by means of the actuators.

11 Claims, 3 Drawing Sheets

DEVICE FOR SIMULATING CRASH SCENARIOS

CROSS REFERENCE TO RELATED APPLICATION

This application claims priority from German Patent Application No. 10 2012 023 076.1, filed Nov. 26, 2012, which is incorporated herein by reference.

BACKGROUND OF THE INVENTION

1. Field of the Invention

The present invention relates to a device for simulating crash scenarios. Such devices are especially used for simulating the effects of a crash on a test object and are also referred to as crash test sled devices.

2. Description of Related Art

In order to test the crash behavior of vehicles and the effects of the impact on specific parts of the vehicle, crash tests with complete vehicles have always been made. For this, the vehicles are accelerated and caused to collide with stationary obstacles. This has normally the effect that the vehicle in question is destroyed completely. Crash tests with complete vehicles are, by nature, very expensive. Therefore, so-called crash sleds have already been used for quite some time. A difference is made between acceleration sleds and deceleration sleds. Deceleration sleds are carefully accelerated to a specific speed by means of a suitable accelerating device and are then decelerated comparatively abruptly by a decelerating unit so as to simulate the impact. When a so-called acceleration sled is used, the impact is, however, simulated inversely. The sled is first standing still and is then accelerated backwards by a very powerful accelerating unit. In either case, the vehicle superstructures to be tested are installed on the sled.

Simple crash sled devices can only reproduce accelerations acting in an axial direction. In most crashes, the acceleration behavior will, however, be complex. The vehicle not only undergoes strong negative acceleration in the longitudinal direction. Depending on how the vehicle collides with the obstacle, also pitching, yawing and rolling movements will occur.

A crash sled device, by means of which pitching as well as yawing movements can be simulated, is known, e.g., from DE 102007056572 A1. The crash sled of this device comprises a lower part and an upper part serving as a carrier for the components to be tested. The upper part rests at the front and at the rear end of the sled on a respective traverse member. The two traverse members can be vertically adjusted independently of one another by means of actuators, so that a pitching movement can be imparted to the upper part of the sled. The upper part of the sled and the two traverse members are supported in sliding contact with one another. The upper part can therefore be moved on the traverse members in a transverse direction. For this, appropriate actuators are provided at the front end as well as at the rear end of the sled. The front end and the rear end of the upper part can thus be moved in a transverse direction independently of one another. A yawing movement about the vertical axis of the sled can be generated in this way. A rolling movement can, however, not be simulated. Moreover, tests have shown that the device disclosed in DE 102007056572 A1 is unsuitable for heavy test objects and great impact loads.

Also DE 102007042775 A1 discloses a two-part crash sled. The upper platform of the sled is configured such that it is able to execute a pitching movement relative to the lower part. For this, two actuators are provided, by means of which the front end and the rear end of the upper platform can be vertically adjusted independently of each other. The device is not suitable for simulating yawing or rolling of the upper platform. A similar device is known from DE 102005010189 B3.

Also the crash sled devices according to DE 19857429 A1 and DE 10118682 B4 allow a pitching movement of the sled. In both cases, the actuators used for vertically adjusting the front and the rear end of the crash sled are either partly or fully integrated in the base and are therefore not disposed between the upper part and the lower part of the sled. Also these devices are unsuitable for simulating yawing or rolling movements.

DE 19805512 B4 discloses a two-part acceleration sled provided with a tilting mechanism in the form of a passive hydraulic unit. The hydraulic unit allows a pitching movement of the upper part of the sled, the forces occurring during the pitching movement being partially absorbed. The publication describes that e.g. a rotational movement of the test setup about the vertical axis of the sled can be superimposed on the pitching movement. A suitable device configured for simulating pitching and yawing movements is, however, not shown.

EP 2098850 A2 discloses a sled for executing crash tests with a dummy. The dummy is secured in position on a platform which is capable of carrying out a secondary movement relative to the actual sled, said secondary movement being superimposed on the impact deceleration. For generating the secondary movement, an actuator unit is provided between the dummy platform and the sled. The sled shown in EP 2098850 A2 is, however, not suitable for heavy test objects and great impact loads.

SUMMARY OF THE INVENTION

In some embodiments, the present invention provides a device comprising a sled that is adapted to be accelerated in the longitudinal direction. The sled comprises a lower part and an upper part supported on the lower part and used as a carrier for the test object. The lower part and the upper part have actuators provided between them, by means of which pitching and yawing movements of the upper part can be generated.

In some embodiments, the present invention provides a device for simulating crash scenarios, in particular for simulating the effects of a crash on a test object, comprising a sled, which is adapted to be accelerated in the longitudinal direction and which comprises a lower part as well as an upper part supported on the lower part and used as a carrier for the test object, the lower part and the upper part having actuators provided between them, by means of which pitching and yawing movements of the upper part can be generated, wherein on an impact-side front end of the sled, the upper part is propped against the lower part by means of a coupling rod which is rotatably coupled on both sides thereof, at least five actuators being provided between the lower part and the upper part, and the upper part being supported on the lower part via the actuators and the coupling rod such that a rolling movement of the upper part can additionally be generated by means of the actuators.

In some embodiments, the present invention provides a sled (2) for a device (1) used for simulating crash scenarios, wherein the sled (2) comprises a lower part (3) as well as an upper part (4) supported on the lower part (4) and used as a carrier for a test object, the lower part (3) and the upper part (4) having actuators (5.1, 5.2, 6.1, 6.2, 7) provided between them, by means of which pitching and yawing movements of the upper part (4) can be generated, wherein on an impact-side front end (8) of the sled (2), the upper part (4) is propped against the lower part (3) by means of a coupling rod (10) which is rotatably coupled on both sides thereof, at least five actuators (5.1, 5.2, 6.1, 6.2, 7) being provided between the lower part (3) and the upper part (4), and the upper part (4) being supported on the lower part (3) via the actuators (5.1, 5.2, 6.1, 6.2, 7) and the coupling rod (10) such that a rolling movement of the upper part (4) can additionally be generated by means of the actuators (5.1, 5.2, 6.1, 6.2, 7)

BRIEF DESCRIPTION OF THE DRAWINGS

Further details and advantages of the present invention shall become apparent from the following description in combination with the drawings. In the following, an embodiment of the present invention will be explained in more detail making reference to drawings, in which.

In the statements following hereinbelow, identical parts will be identified by identical reference numerals. If a figure should contain reference numerals which are not mentioned in the associated description of the figure, reference is made to preceding or subsequent descriptions of figures.

DETAILED DESCRIPTION

Figure 1:
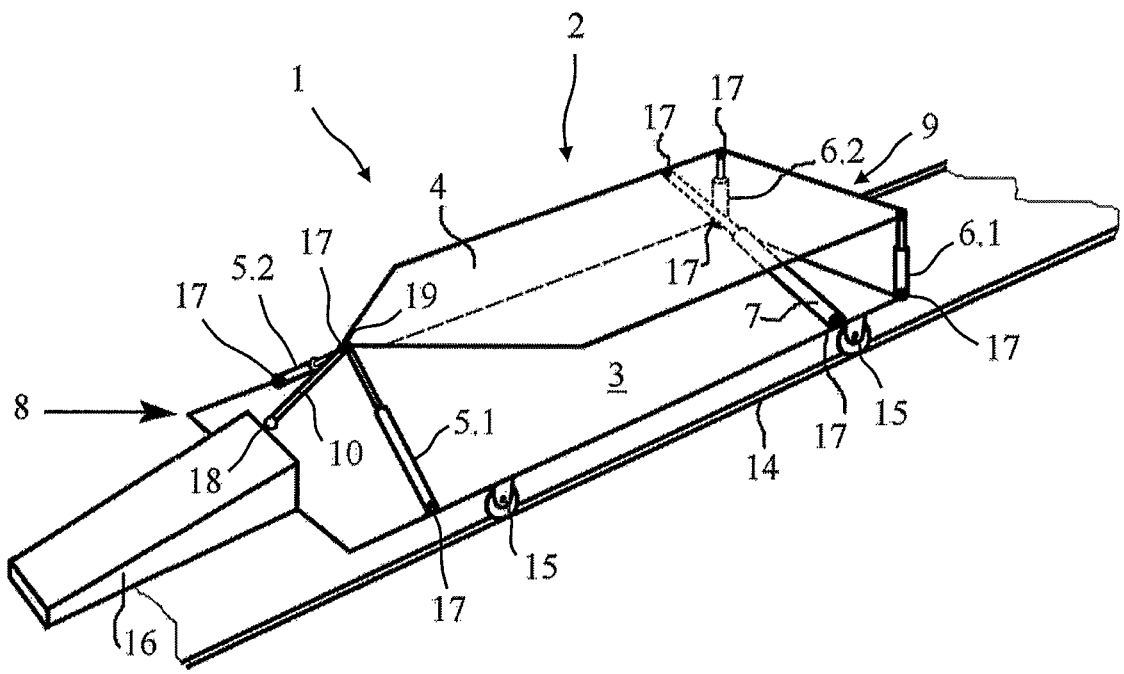
FIG. 1 shows an oblique view of the sled of a device according to the present invention.

It is the object of the present invention to provide a device as described herein, by means of which pitching as well as yawing and rolling movements can be superimposed on the simulated impact deceleration. The device should additionally have a simple structural design and it should be robust and reliable. Furthermore, the device should be suitable for heavy test objects.

This object is achieved by the features of the independent claim 1. According to these features, a solution according to the present invention exists in the case of a device of the type referred to at the beginning, when, on an impact-side front end of the sled, the upper part of the sled is propped against the lower part by means of a coupling rod which is rotatably coupled on both sides thereof, at least five actuators being provided between the lower part and the upper part, and the upper part being supported on the lower part via the actuators and the coupling rod such that a rolling movement of the upper part can additionally be generated by means of the actuators.

The invention offers the advantage that all the accelerations occurring during a real crash can be simulated. The solution according to the present invention guarantees that the crash sled device is suitable also for heavy test objects. The extremely high forces generated in the longitudinal direction of the sled in response to an impact are absorbed through the coupling rod provided between the upper part and the lower part. The coupling rod is therefore oriented such that, at the starting position of the sled, it extends substantially parallel to the longitudinal axis of the sled or at least parallel to the central longitudinal plane of the sled. The coupling rod is preferably arranged centrally and extends therefore in the central longitudinal plane of the sled. Hence, the actuators need not absorb the forces generated in the longitudinal direction of the sled in response to an impact. This guarantees, on the one hand, that the functionality of the actuators will not be impaired and, on the other hand, that the actuators can be configured as comparatively light and space-saving components. The invention thus provides a compact and simultaneously robust and reliable crash sled device. The light and compact structural design of the sled leads, in turn, to a higher load capacity. Comparatively heavy test objects can be tested by means of a light crash sled.

According to a specially preferred embodiment of the present invention, the coupling rod as well as the actuators are each articulated on the lower part and the upper part via a respective bearing having at least two rotational degrees of freedom. Preferably, the bearings have three rotational degrees of freedom. It is thus guaranteed that the upper part of the sled can be rotated and tilted relative to the lower part in any imaginable direction. If bearings having three rotational degrees of freedom are used, complicated and expensive slide guide means will not be necessary. According to another preferred embodiment, the bearings are configured as ball-and-socket joints. If bearings having only two rotational degrees of freedom are used, actuators having themselves a rotational degree of freedom may be used alternatively. For example, hydraulic actuators may be used, whose piston is supported in the cylinder such that the piston can be rotated about its own axis.

According to a further specially preferred embodiment of the present invention, the lower part and the upper part of the sled have arranged between them two actuators on the front end of the sled and three actuators on the opposite rear end of the sled. Hence, this embodiment only necessitates the use of five actuators for superimposing all imaginable rotational movements in the form of pitching, yawing or rolling movements on the deceleration in the longitudinal direction of the sled. In addition, the structural design of the sled is very simple according to this embodiment, and it allows easy control of the actuators.

According to this embodiment it will additionally be of advantage when the two actuators at the front end of the sled always enclose an angle relative to one another at any position. Preferably, the two actuators enclose an obtuse angle. Further preferred, the two front actuators are rotatably articulated on the two longitudinal sides of the sled and extend upwards towards each other at an oblique angle, so that the two upper points of articulation on the upper part meet at a shared point or in a shared area of application. Preferably, also the coupling rod is articulated on the upper part in this shared area of application. According to this embodiment, a particularly advantageous transmission of force at the front end of the sled as well as a particularly simple control of the two front actuators is accomplished.

In the case of the embodiment comprising two actuators at the front end of the sled and three actuators at the rear end, it will additionally be of advantage when two of the three actuators are arranged at the rear end on the two opposed longitudinal sides of the sled and are oriented substantially vertically when occupying a starting position, the third one of these three actuators being articulated on the lower part on one of the two longitudinal sides of the sled, and on the upper part on the opposite longitudinal side of the sled. Also this leads to a particularly light structural design of the sled and a particularly easy control of the actuators.

According to another specially preferred embodiment of the present invention, the actuators are configured as hydraulic cylinders. In this way, a precise and fast movement of the upper part is accomplished. In addition, very strong forces can be generated by means of hydraulic cylinders, and, consequently, very heavy test objects can be tested. The hydraulic system for supplying the hydraulic cylinders is accommodated on board the sled and is equipped with a pressure accumulator that is recharged after each individual test.

According to a further specially preferred embodiment of the present invention, the sled is configured as a deceleration sled. In principle, the invention is also adapted for use with acceleration sleds, which simulate the impact inversely. The embodiment comprising the deceleration sled, however, allows testing of particularly large test objects making use of a deceleration method.

The invention additionally provides a sled for a device used for simulating crash scenarios.

FIG. 1 shows the crash sled 2 of a device 1 according to the present invention in an oblique view. The sled is provided with wheels 15 and can be accelerated to a specific initial speed by means of an accelerating device, which is not shown, in the rail system 14. The device additionally comprises a braking unit, which is not shown either, and which decelerates the sled in accordance with an actual crash time deceleration function. For this, a plurality of commercially available braking systems exist. In the present case, the device is provided with a so-called hydrobrake. For this purpose, the front end 8 of the sled 2 has attached thereto a so-called brake wedge 16, which, for simulating the impact at the end of the rail path 14, enters the gap between two brake rollers that are pressed against each another. In order to be able to reproduce given deceleration functions, the force with which the two brake rollers are pressed against each other is controllable.

Figure 2:
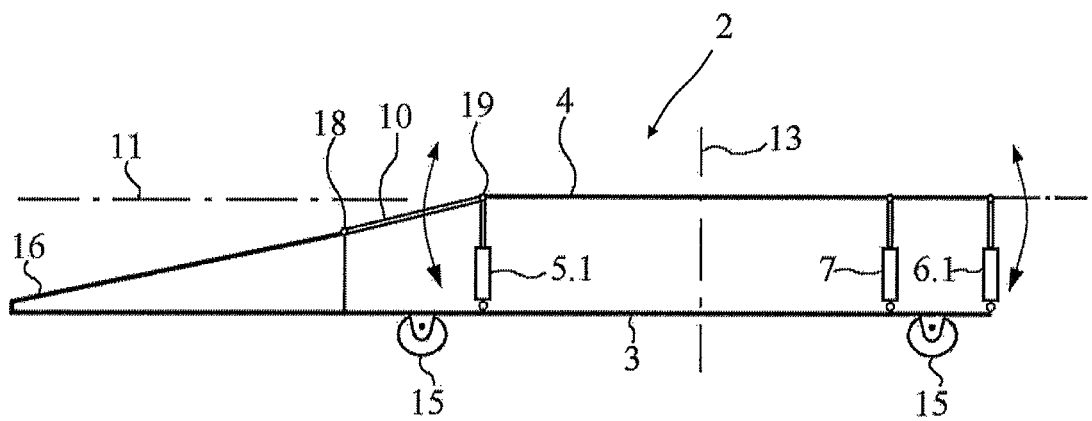
FIG. 2 shows the sled according to FIG. 1 in a side view.
Figure 3:
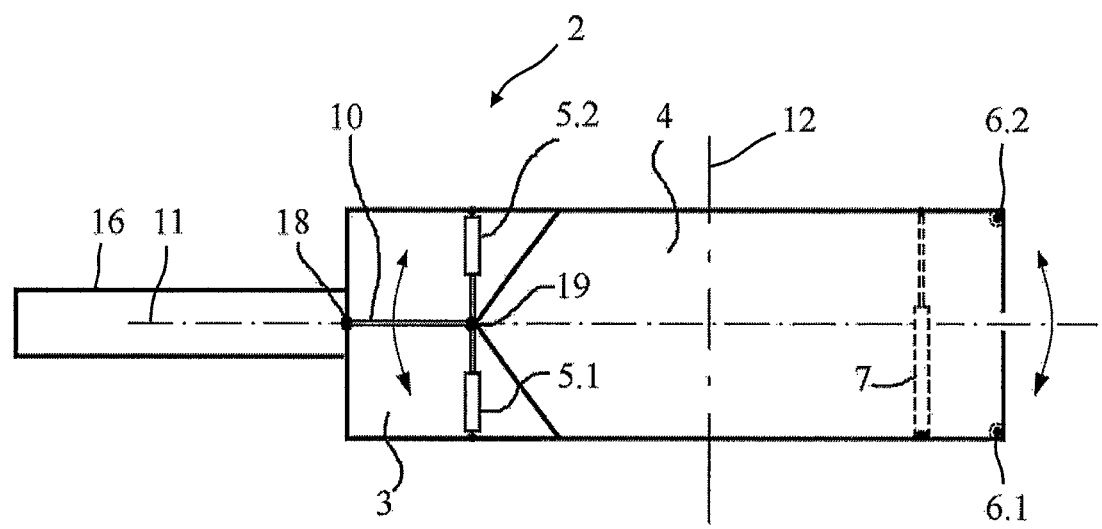
FIG. 3 shows the sled according to FIGS. 1 and 2 in a top view.
Figure 4:
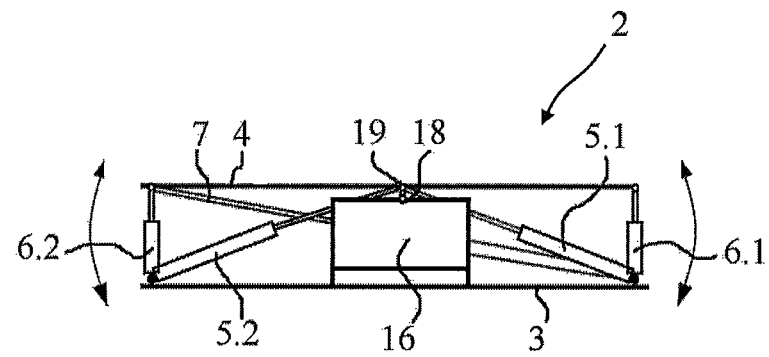
FIG. 4 shows the sled according to FIGS. 1-3 in a front view.

The crash sled 2 is bipartite and comprises thus a lower part 3 and an upper part 4. The lower part 3 has the wheels 15 attached thereto. Also the brake wedge 16 is rigidly connected to the lower part 3 of the sled. The upper part 4 is used as a platform for the test setup. This means that the test objects to be tested are mounted on the upper part 4 of the sled. The upper part 4 is supported such that it is movable relative to the lower part 3. The movable support is established exclusively via the coupling rod 10 at the front end 8 of the sled and via the five actuators 5.1, 5.2, 6.1, 6.2 and 7. The coupling rod 10 essentially serves to axially prop the upper part 4 against a rigid support element of the lower part 3 on the front end 8 of the sled. The coupling rod 10 is rotatably supported on the lower part 3 as well as on the upper part 4 via a respective ball-and-socket joint 18 and 19. The bearing 18 on the side of the lower part is located behind the brake wedge 16. Reference should here be made to the fact that all the figures are of a schematic nature. Other than shown in the figure, the bearing 18 may be disposed on a support bracket, which is specially provided for this purpose. The side view in FIG. 2, the top view in FIG. 3 and the front view in FIG. 4 show that, at the starting position, the coupling rod 10 is located at the longitudinal center plane of the sled. At this starting position, it extends not quite parallel to the longitudinal axis 11 of the sled shown in FIG. 2. Like bearing 18, bearing 19, through which the coupling rod is connected to the upper part 4 of the sled, is configured as a ball-and-socket joint. The coupling rod is therefore supported such that pitching movements of the upper part about the transverse axis 12 shown in FIG. 3 as well as yawing movements about the vertical axis 13 shown in FIG. 2 and rolling movements about the longitudinal axis 11, which is also shown in FIG. 2, are possible. Reference is also made to the fact that the axes 11, 12 and 13 are not solid axles but imaginary axes, which, depending on the position of the upper part 4, migrate together with the upper part. The two bearings 18 and 19 may also be configured as pivot joints having only two rotational degrees of freedom. In this case, the coupling rod 10 must, however, be configured such that the rear end of the coupling rod can be rotated relative to the front end thereof. This can be realized e.g. with a bipartite coupling rod whose front part is connected to the rear part via a conventional roller bearing.

The displacement of the upper part 4 about the longitudinal axis 11, the transverse axis 12 and the vertical axis 13 is executed by means of the five actuators 5.1, 5.2, 6.1, 6.2 and 7. Each of the actuators is connected via a respective ball-and-socket joint 17 with the lower part 3 as well as with the upper part 4 of the sled. The actuators are hydraulic cylinders that are driven via a hydraulic system, which is not shown and which is carried along on board the sled. The hydraulic system is equipped with a pressure accumulator that has to be recharged before each individual test. The two hydraulic cylinders 5.1 and 5.2 at the front end 8 of the sled are supported substantially at the two opposed longitudinal sides of the lower part 3 and extend towards each other at an oblique angle. The longitudinal axes of these two actuators enclose an obtuse angle. Both actuators are supported on the upper part 4 in the same area as the coupling rod 10. The bearing 19 of the coupling rod 10 as well as the two upper bearings of the actuators 5.1 and 5.2 are therefore located close to one another.

Two additional actuators 6.1 and 6.2 are provided at the rear end 9 of the sled in the two opposed rear corners. A fifth actuator 7 is also arranged on the rear end 9 of the sled and extends transversely to the longitudinal axis 11 from the lower part 3 of the sled at an oblique angle upwards to the upper part 4. The lower bearing of the fifth actuator 7 is located on the left longitudinal side of the sled, and the upper bearing is located on the right longitudinal side thereof.

The rear end of the upper part 4 can be moved in a transverse direction by means of the actuator 7. The two front actuators 5.1 and 5.2 are responsible for moving the front end of the upper part in a transverse direction. If, for example, the cylinder of the right actuator 5.2 is retracted and the cylinder of the left actuator 5.1 is simultaneously extended, the front end of the upper part will move to the right in a transverse direction. By means of the two front actuators 5.1 and 5.2, the front end of the upper part can also be displaced vertically. The vertical displacement of the rear end is executed by means of the two rear actuators 6.1 and 6.2. Although all actuators cooperate, a pitching movement of the upper part is therefore mainly generated by a displacement of the actuators 5.1, 5.2, 6.1 and 6.2. What matters with respect to a yawing movement is primarily a displacement of the actuators 5.1, 5.2 and 7. Finally, a rolling movement takes place, when the actuators 6.1 and 6.2 are operated in opposite directions.

Figure 5:
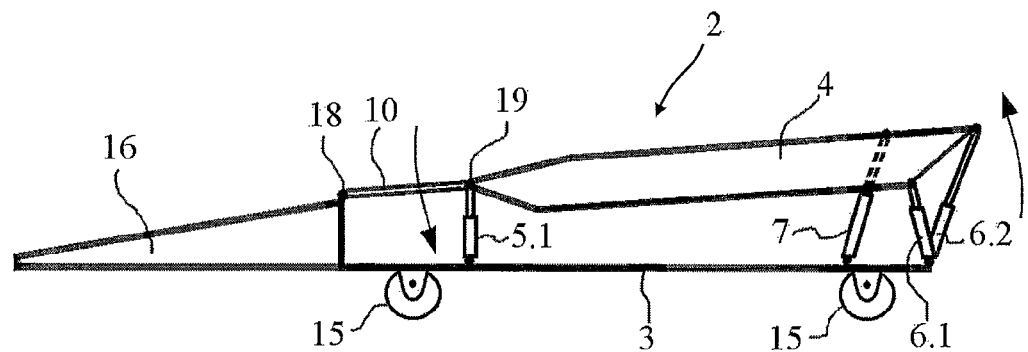
FIG. 5 shows a side view of the sled according to FIGS. 1-4, with the upper part deflected.
Figure 6:
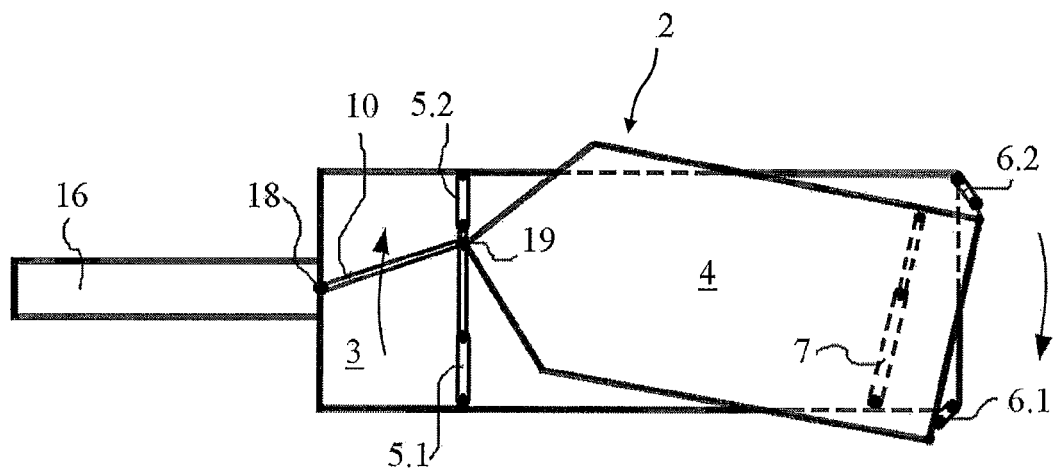
FIG. 6 shows a top view of the sled according to FIG. 5.
Figure 7:
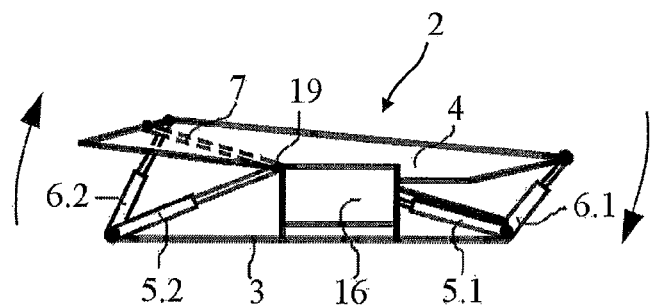
FIG. 7 shows a front view of the sled according to FIGS. 5 and 6.

FIGS. 5-7 show the sled 2 at the end of an impact simulation. The upper part 4 of the sled has been deflected from the starting position shown in FIGS. 1-4. During the simulation, a combined pitching, yawing and rolling movement has been imparted to the upper part 4. In so doing, the combined tilting has been superimposed on the axial deceleration function.

It is pointed out that also pivot bearings having each only two rotational degrees of freedom may be used for supporting the actuators 5.1, 5.2, 6.1, 6.2 and 7, provided that the actuators themselves allow rotation. In the case of hydraulic cylinders, e.g., the piston may be supported such that it is rotatable relative to the cylinders.

The invention claimed is:

1. A device (1) for simulating crash scenarios, in particular for simulating the effects of a crash on a test object, comprising a sled (2), which is adapted to be accelerated in the longitudinal direction and which comprises a lower part (3) as well as an upper part (4) supported on the lower part (3) and used as a carrier for the test object, the lower part (3) and the upper part (4) having actuators (5.1, 5.2, 6.1, 6.2, 7) provided between them, by means of which pitching and yawing movements of the upper part (4) can be generated, wherein on an impact-side front end (8) of the sled (2), the upper part (4) is propped against the lower part (3) by means of a coupling rod (10) which is rotatably coupled on both sides thereof, at least five actuators (5.1, 5.2, 6.1, 6.2, 7) being provided between the lower part (3) and the upper part (4), and the upper part (4) being supported on the lower part (3) via the actuators (5.1, 5.2, 6.1, 6.2, 7) and the coupling rod (10) such that a rolling movement of the upper part (4) can additionally be generated by means of the actuators (5.1, 5.2, 6.1, 6.2, 7), wherein at least at a starting position of the sled the coupling rod extends substantially in a central longitudinal plane of the sled, the coupling rod being a rigid component able to absorb forces generated in the event of a simulated crash in the longitudinal direction of the sled such that the actuators need not absorb forces generated in the longitudinal direction.

2. The device (1) according to claim 1, characterized in that the coupling rod (10) and the actuators (5.1, 5.2, 6.1, 6.2, 7) are each articulated on the lower part (3) and the upper part (4) via a respective bearing (17, 18, 19) having at least two rotational degrees of freedom.

3. The device (1) according to claim 2, wherein the bearings (17, 18, 19) have three rotational degrees of freedom.

4. The device (1) according to claim 3, wherein the bearings (17, 18, 19) are configured as ball-and-socket joints.

5. The device (1) according to claim 2, wherein the actuators (5.1, 5.2, 6.1, 6.2, 7) themselves have a rotational degree of freedom.

6. The device (1) according to claim 1, characterized in that the lower part (3) and the upper part (4) have arranged between them two actuators (5.1, 5.2) on the front end (8) of the sled (2) and three actuators (6.1, 6.2, 7) on the opposite rear end (9) of the sled (2).

7. The device (1) according to claim 6, wherein the two actuators (5.1, 5.2) on the front end (8) always enclose an angle relative to one another at any position.

8. The device (1) according to claim 6, wherein two of the three actuators (6.1, 6.2, 7) are arranged at the rear end (9) on the two opposed longitudinal sides of the sled (2) and are oriented substantially vertically when occupying a starting position, the third one of these three actuators (6.1, 6.2, 7) being articulated on the lower part (3) on one of the two longitudinal sides of the sled (2) and on the upper part (4) on the opposite longitudinal side of the sled (2).

9. The device (1) according to claim 1, wherein the actuators (5.1, 5.2, 6.1, 6.2, 7) are configured as hydraulic cylinders.

10. The device (1) according to claim 1, wherein the sled (2) is configured as a deceleration sled.

11. A sled (2) for a device (1) used for simulating crash scenarios, wherein the sled (2) comprises a lower part (3) as well as an upper part (4) supported on the lower part (3) and used as a carrier for a test object, the lower part (3) and the upper part (4) having actuators (5.1, 5.2, 6.1, 6.2, 7) provided between them, by means of which pitching and yawing movements of the upper part (4) can be generated, wherein on an impact-side front end (8) of the sled (2), the upper part (4) is propped against the lower part (3) by means of a coupling rod (10) which is rotatably coupled on both sides thereof, at least five actuators (5.1, 5.2, 6.1, 6.2, 7) being provided between the lower part (3) and the upper part (4), and the upper part (4) being supported on the lower part (3) via the actuators (5.1, 5.2, 6.1, 6.2, 7) and the coupling rod (10) such that a rolling movement of the upper part (4) can additionally be generated by means of the actuators (5.1, 5.2, 6.1, 6.2, 7), wherein at least at a starting position of the sled the coupling rod extends substantially in a central longitudinal plane of the sled, the coupling rod being a rigid component able to absorb forces generated in the event of a simulated crash in a longitudinal direction of the sled such that the actuators need not absorb forces generated in the longitudinal direction.

* * * * *

UNITED STATES PATENT AND TRADEMARK OFFICE
CERTIFICATE OF CORRECTION

| | |
|---|---|
| PATENT NO. | : 9,212,973 B2 |
| APPLICATION NO. | : 14/088974 |
| DATED | : December 15, 2015 |
| INVENTOR(S) | : Robert Weber |

It is certified that error appears in the above-identified patent and that said Letters Patent is hereby corrected as shown below:

IN THE CLAIMS

Column 7, Line 23, Claim 2, delete "characterized in that" and insert -- wherein --

Column 7, Line 35, Claim 6, delete "characterized in that" and insert -- wherein --

Signed and Sealed this
Twenty-sixth Day of April, 2016

Michelle K. Lee
*Director of the United States Patent and Trademark Office*